United States Patent [19]

Henderson et al.

[11] 4,393,045
[45] Jul. 12, 1983

[54] COSMETIC COMPOSITION

[76] Inventors: Esther G. Henderson; Inger V. Mallet, both of 2521 Main St., Baton Rouge, La. 70802

[21] Appl. No.: 316,111

[22] Filed: Oct. 29, 1981

[51] Int. Cl.$^3$ .................. A01N 63/02; A61K 35/12
[52] U.S. Cl. ............................................ 424/95
[58] Field of Search .................................. 424/95, 59

[56] References Cited

U.S. PATENT DOCUMENTS 3,624,201  11/1971  Balassa .................................. 424/95

OTHER PUBLICATIONS

Jpn. Kokai Tokkyo Koho, 80 133 401, published Oct. 17, 1980, as abstracted in Chemical Abstracts, vol. 94, 1981.

*Primary Examiner*—Elbert L. Roberts
*Attorney, Agent, or Firm*—Frederick A. Stolzle, Jr.

[57] ABSTRACT

Curative, cosmetic compositions having healing and remedial properties on skin afflictions such as acne and burns when applied topically to humans. The compositions are formed by contacting the extrudate of a citric acid containing fruit with the mother of pearl portion of a mollusk shellfish.

6 Claims, No Drawings

COSMETIC COMPOSITION

INTRODUCTION

Efforts to mitigate or cure the scarring effects of skin trauma and afflictions such as acne and burns have persisted for centuries. Acne, burns and other skin afflictions such as rashes are not only painful in their active stages but they can also leave permanent physical as well as psycological scars. With respect to acne, of the myriads of topical preparations available, those containing benzoyl peroxide and or sulfur are currently in favor. However, hypersensitivity is a common problem associated with the use of these chemical preparations and this hypersensitive reaction often precludes their use and/or diminishes their effectiveness.

The present invention provides a natural, organic, curative, cosmetic composition which facilitates the curing and healing of skin afflictions such as acne, burns, blisters, cuts, sores and the like. Furthermore, because the compositions of this invention are natural and organic the problem of hypersensitivity associated with the inorganic preparations is diminished significantly. Additionally, compositions of the present invention mitigate the acne and burn related symptoms of pain, swelling and scarring.

SUMMARY OF THE INVENTION

The present invention provides a curative, cosmetic composition formed by intimately admixing the extrudate of a citric acid containing fruit with the inner lining of a mollusk shell, said composition having healing properties on a variety of skin afflictions when applied topically to humans. In a preferred embodiment said admixing is accomplished by contacting the crushed inner lining of a mollusk shell (known as mother of pearl) with the extrudate of a citric acid containing fruit. The resulting curative composition, when applied topically to the afflicted area displays remarkable healing properties without irritation and hypersensitivity sometimes associated with acne medications now in popular use.

DESCRIPTION OF THE PREFERRED EMBODIMENTS

Compositions of the invention are preferably formed by intimately admixing the citric acid containing fruit extract with the lining (mother of pearl) of a mollusk shellfish. It has been found that the admixing or commingly is best effected by contacting the particularly or crushed mother of pearl of the shellfish with the citric acid containing extract. Mother of pearl can be purchased commercially at a variety of outlets in this country. The mother of pearl is then crushed by means well known in the art such as mechanical blending, pulverizing, motar and pestal and the like. Preferably the mother of pearl is crushed to powder form which facilitate interaction and commingling with the juice and speeds up the reaction. Normally equal parts by weight of the powdered mother of pearl and the strained juice are intimately mixed also by means well known in the art such as stirring, blending and the like.

Blending is continued until the bubbling reaction ceases usually from about 1/15 hours to about ½ hours. The time period for blending may vary according to the absolute amount of mother of pearl and juice blended.

After blending is completed, the composition is allowed to dry to the consistency or viscosity desired. Preferably the composition is allowed to dry in the sun, although other expedients well known in the art such as dessication, roto-vaporation and the like may be employed.

The composition is dried to a paste-like viscosity so that it may be applied as a moist mask to the afflicted area.

Use of the compositions of this invention involving application of a thin layer of the composition to the afflicted area. The mask is left on the area until it dries and can remain on the area for periods of time of from about 1/6 hours to 12 hours or as needed. The process is repeated as needed or desired.

Webster's Seventh New Collegiate Dictionary, G. & C. Merriam Company, 1969, defines Mother of pearl as the hard pearly iridescent substance forming the inner layer of a mollusk shell. Mollusk is defined as any of a large phylum (Mollusca) of invertebrate animals (as snails or clams) with a soft unsegmented body usually enclosed in a calcareous shell: (broadly: SHELLFISH). Calcareous is defined as consisting of or containing calcium carbonate.

While mollusca shellfish lining such as oyster, clam, abilone, the turbo family (gold turbo, silver turbo) and the nautilaus family may be employed in the practice of this invention preferred are the black lipped, gold lipped and penguin oyster mother of pearl. Particularly preferred is the "black lipped" mother of pearl.

Preferred citric acid containing fruits used in the practice of this invention include the lime, lemon, orange, grapefruit and tangerine. Particularly preferred is the lime.

In obtaining the extrudate of the citric acid containing fruit the juice is removed from the fruit by conventional means such as mechanical squeezing. The juice is then strained or filtered preferrably twice to remove excessive pulp, seeds and the like.

Various stabilizers, coloring agents, scenting agents and the like may be added to the compositions of this invention if desired. For example, extract of coconut, peppermint and mint can be admixed with compositions of this invention. For Example, McCormick, Registered Trademark, Imitation Coconut Extract, McCormick & Co., Inc., Baltimore, Md. containing water, 25%/wt. alcohol, propylene glycol, vanillin, gamma nonalactone and other lactones, diacetyl, and ethyl heptoate; and McCormick, Registered Trademark, Pure Mint, and Peppermint Extract—Alcohol 85%, water, oil of spearmint, oil of peppermint, and extractives of spearmint leaves can be added in amounts ranging from 0.001 percent by weight to about 0.1 percent by weight of the composition of this invention. Such admixture has been found to improve the smell of the composition as well as lenghtening shelf life.

The following non-limiting examples illustrate and particularly point out methods of preparing and use of some of the compositions of this invention.

EXAMPLE I

PREPARATION OF A COMPOSITION OF THE INVENTION

A quantity of particulated black lipped mother of pearl was obtained from a commerical source and was ground to a fine powder with a mortar and pestal. 15 Grams of the powdered black lipped mother of pearl were added to an open graduated flask and 15 grams of lime juice were added to the powder. The mixture was stirred for 5 minutes with a magnetic stirrer and a foaming reaction was observed. The white composition was allowed to partially dry in sunlight at ambient temperatures of about 28° to 30° C. for a period of 24 hours. The resulting liquid, viscous composition was white in color and had the consistency of cream.

EXAMPLE II

APPLICATION OF A COMPOSITION OF THE INVENTION

A subject afflicted with acne applied a thin mask of the viscous composition to one side of her face. The mask was allowed to remain on her face overnight. The routine of applying the composition of this invention to the same side of her face overnight was repeated for a period of seven nights. After the seven day period a noticable improvement (i.e. a reduction of 45% of eruptions) of the acne on the side of the face treated was observed. After 14 days a reduction of about 75% of eruptions was observed. Furthermore, the pain associated with the acne was mitigated.

EXAMPLE III

PREPARATION OF A COMPOSITION OF THE INVENTION

20 Grams of the strained extract of a lemon were poured into the concave inner lining of a polished "Donkey Ear" abilone. A foaming reaction was observed. The mixture was allowed to react for 18 hours with intermittent rubbing and scraping the inner lining to facilitate contact of the lemon extrudate with the mother of pearl lining. 256 Grams of the resulting brownish liquid composition was poured into an open flask and allowed to partially dry to a paste-like consistency. 2 Grams of coconut extract were mixed with the paste-like composition.

EXAMPLE IV

APPLICATION OF A COMPOSITION OF THE INVENTION

The composition prepared in Example III was applied to a subject who had recently received a second-degree blister burn. After three days of continuous use remarkable improvement of the burn was noticed including drying of the blisters and shrinkage of the area of the burn.

EXAMPLE V

The procedure of Example I was followed using Gold turbo mother of pearl. The resulting composition was tan and viscous.

EXAMPLE VI

The procedure of EXAMPLE I was followed using Donkey Ear abilone. The resulting composition was white and viscous.

EXAMPLE VII

The procedure of Example I was followed using Louisiana oyster shell. The resulting composition was off-white in color.

What is claimed is:

1. A curative, cosmetic composition formed by intimately admixing the extrudate of a citric acid containing fruit with the inner lining of a mollusk shell, said composition having healing properties on a variety of skin afflictions when applied topically to humans.

2. A composition of claim 1 where said admixing is accomplished by contacting the crushed inner lining of said mollusk shell with said extrudate.

3. A composition of claim 1 wherein said admixing is accomplished by placing the extrudate of a citric acid containing fruit in the concave interior of said mollusk shell followed by intermittant mechanical agitation of said extrudate.

4. A composition of claim 1 wherein said admixing is affected in the presence of sunlight.

5. A composition of claim 1 wherein said citric acid containing fruit is selected from the group consisting of lemon, lime, orange, grapefruit, tangerine and satsuma.

6. A composition of claim 1 wherein said mollusk shell is selected from the group consisting of oyster, clam and abilone.

* * * * *